United States Patent [19]

Ellis, Jr. et al.

[11] Patent Number: 5,659,029

[45] Date of Patent: Aug. 19, 1997

[54] PREPARATION OF PORPHYRINS AND THEIR METAL COMPLEXES

[75] Inventors: Paul E. Ellis, Jr., Downingtown, Pa.; Wayne A. Langdale, Wenonah, N.J.

[73] Assignee: Sun Company, Inc. (R&M), Philadelphia, Pa.

[21] Appl. No.: 575,783

[22] Filed: Dec. 22, 1995

[51] Int. Cl.$^6$ .................................................. C07D 487/22
[52] U.S. Cl. ........................................ 540/145; 548/400
[58] Field of Search ............................ 540/145; 548/400

[56] References Cited

U.S. PATENT DOCUMENTS

| | | | |
|---|---|---|---|
| 3,076,813 | 2/1963 | Sharp et al. | 540/145 |
| 3,579,533 | 5/1971 | Valman | 260/314 |
| 4,895,680 | 1/1990 | Ellis et al. | 260/410.9 |
| 4,895,682 | 1/1990 | Ellis et al. | 260/410.9 |
| 4,900,871 | 2/1990 | Ellis et al. | 568/399 |
| 4,970,348 | 11/1990 | Ellis et al. | 568/399 |

OTHER PUBLICATIONS

Ellis, et al., Cat. Lett., 3, 389 (1991).
Lyons, et al., Cat Lett., 8, 45 (1991).
MacRobert, et al., Chem. and Ind., p. 17 (Jan. 6, 1992).
Krol., J. Org. Chem., Dec. 1959, p. 2066., vol. 24.

*Primary Examiner*—Mukund J. Shah
*Assistant Examiner*—Pavanaram K. Sripada
*Attorney, Agent, or Firm*—Stephen T. Falk; Q. Todd Dickinson

[57] ABSTRACT

A hydroxyl-containing pyrrolic compound having a hydroxyl group or a hydroxyl-containing group in the 2-position, optionally substituted in the beta positions, is condensed in an acidified two immiscible phase solvent system to produce excellent yields of the corresponding porphyrin or metal porphyrin.

27 Claims, No Drawings

PREPARATION OF PORPHYRINS AND THEIR METAL COMPLEXES

The Government of the United States has rights in this invention under Department of Energy Contract No. DE-FC21-90MC26029.

This invention provides an improved process for the preparation of porphyrins and metal complexes thereof. Synthetic porphyrins and metal porphyrins have many uses including as oxidation catalysts (Ellis and Lyons, Cat. Lett. 3, 389 [1991]; Lyons and Ellis, Cat. Lett. 8, 45 [1991]; U.S. Pat. Nos. 4,895,680; 4,895,682; 4,900,871; 4,970,348), sensitizers for photodynamic therapy (MacRobert and Phillips, Chem. and Ind., Jan. 6, 1992, p. 17), and organic dyes.

Many procedures or synthetic schemes are known for preparation of porphyrin complexes having the general formula (I):

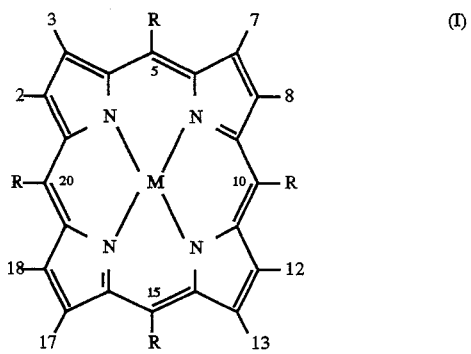

where R is H, hydrocarbyl or halocarbyl and the beta or pyrrolic positions (2, 3, 7, 8, 12, 13, 17, 18) are independently occupied by H, hydrocarbyl or halocarbyl, and M is a metal or $H_2$. When R is H and 2, 3, 7, 8, 12, 13, 17 and 18=H then the porphyrin is known as porphin, or as metal porphin if there is a metal present. When any R or any of 2, 3, 7, 8, 12, 13, 17 or 18 is other than H, the complex is known as a porphyrin or porphine, or as a metal porphyrin or metal porphine if a metal is present. Thus a "porphyrin" has a porphin or porphyrin ring which is either unsubstituted, as in porphin, or substituted as in porphyrins or porphines.

Porphin itself is difficult to produce in high yields and in economically viable quantities. Yalman, U.S. Pat. No. 3,579, 533 (1971) describes a synthesis of copper porphin in yields as high as 20% based on the limiting reagent 2-hydroxymethylpyrrole (2-HMP) at concentrations of 2-HMP of about 0.03M. Yalman's approach was to use large amounts of copper acetate in the condensation reaction and use dimethylformamide (DMF) as the solvent. Other solvents worked poorly for him as did metals other than copper. Yalman's synthesis of porphin suffers from at least three significant problems. The reactions are poorly reproducible as evidenced by Table IV in his patent. Under identical conditions, yields of copper porphin varied from 19.75 to 1.2%. Another problem with the Yalman procedure is the difficulty in isolation of the product. Because of the high boiling point of DMF it is difficult to remove it from the reaction mixture without repeated washes and extractions. A third problem with the Yalman procedure is the difficulty of removing the Cu from CuP since it requires very strongly acid conditions and further lowers the yields of the desired $H_2P$.

Longo et al., *J. Heterocyclic Chem.*, 12, 1305 (1975) disclose preparation of porphin in yields of up to 18% based on 2-HMP, but using dilute solutions (0.0001–0.002M 2-HMP) and two week reaction times. At more economically attractive concentrations (0.01M) the yield falls to 4% overall.

Kuroda et al, "A New Route for Meso-Substituted Porphyrin", *Tetrahedron Letters*, vol. 30, No. 18, pp 2411-2, 1989, disclose the use of propionic acid as solvent in synthesis of meso-substituted $H_2$ or Zn porphyrins from 2-acylpyrroles.

DESCRIPTION OF THE INVENTION

It has been found that a hydroxyl-containing pyrrolic compound such as II, having a hydroxyl group or a hydroxyl-containing group in the 2-position, and optionally substituted in the beta positions, can be condensed in an acid-catalyzed plural immiscible phase solvent system to produce excellent yields of the corresponding porphyrin or metal porphyrin. The following structure shows such a hydroxyl-containing pyrrole:

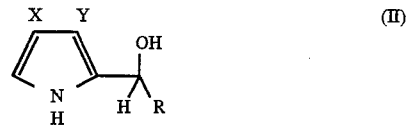

where R is H, hydrocarbyl or halocarbyl and X and Y are independently H, hydrocarbyl or halocarbyl. Typical of these pyrroles are 2-hydroxymethylpyrrole and 2-(1'-hydroxyethyl)pyrrole, from which one obtains porphin and meso-tetramethylporphine respectively. Other pyrrolic hydroxyl compounds which undergo similar reactions may also be used.

"Hydrocarbyl" signifies a group which comprises carbon and hydrogen and may or may not contain other atoms or subgroups. "Halocarbyl" signifies a group which comprises carbon and halogen and may or may not contain hydrogen.

REACTION MIXTURE AND CONDITIONS

The condensation reaction according to the invention is carried out in an acidic two phase solvent system in which the hydroxyl-containing pyrrolic starting material is dissolved in a water-immiscible solvent and added to a phase containing an acid catalyst. Metal complexes can be added to either phase if soluble in one or the other phase, or no metal is added if the desired product is the metal-free porphyrin. The acid used can be carboxylic, such as acetic or propionic and the like, or inorganic such as HBr or HCl, or a complex such as $BF_3$—$C_2H_5OH$ and many others. Copper acetate and other copper salts such as cupric chloride or bromide work well under certain conditions in this reaction. Also zinc and magnesium salts can be used to advantage especially if the zinc or magnesium porphyrin is desired. Many other salts can be used also.

The process of the invention is carried out under conditions in which four molecules of the hydroxyl-containing pyrrolic starting material join in a porphryin ring structure, with evolution of water. The temperature of the reaction can be varied from about 0° C. to about 100° C. After a sufficient reaction time the reaction mixture is oxidized by using a choice of oxidants including molecular oxygen in the form of air or other mixtures of molecular oxygen and other gases such as nitrogen. Other suitable inorganic or organic oxidizing agents as known in the art may be used. Potassium peroxy-monosulfate, for example, or quinones such as chloranil or 2,3-dichloro-5,6-dicyano-1,4-benzoquinone (DDQ), may advantageously be used.

Typical procedure according to the invention is to predissolve the hydroxyl-containing pyrrolic starting material in the organic solvent and to add this solution dropwise over a minimum time of 10 minutes to a rapidly stirred solution of the acid predissolved in water. After 2 hours or so of stirring at room temperature, the oxidant is added and the mixture is heated for a short period of time, if necessary, for better results. The organic phase is then separated, neutralized, and filtered through activated alumina. The solvent is removed, leaving dry and pure porphyrin or metal porphyrin.

PORPHYRIN PRODUCT

The porphyrins prepared according to the invention preferably contain electron-withdrawing atoms or groups in meso and/or beta positions. Such atoms or groups may be substituents on the pyrrole used in the process according to the invention. Alternatively, they may be substituted for hydrogen in the product molecule by known reactions. Preferably such atoms or groups comprise halogen, nitro, cyano, halocarbyl, nitrocarbyl and cyanocarbyl atoms or groups. Preferably, the metal in the catalyst is a transition metal such as iron, cobalt, chromium, manganese, ruthenium or copper. Iron is particularly preferred.

STARTING MATERIAL

Any suitable hydroxyl-containing pyrrolic compound may be used as starting material for the process. Preferably, the starting material has the formula (II) above.

PLURAL-PHASE REACTION MIXTURE

The reaction mixture in the process according to the invention comprises an aqueous phase and an organic phase. The aqueous phase contains an acid catalyst, and the organic phase contains the hydroxyl-containing pyrrolic starting material dissolved in an organic solvent.

ACID CATALYST

The acid in the aqueous phase of the reaction mixture of the process according to the invention may be an organic or inorganic acid. Preferred organic acids are acyclic acids containing 1 to 6 carbon atoms, for example formic acid, acetic acid or propionic acid. Aromatic acids such as benzoic acid and inorganic acids such as HBr or HCl can be used. The acid used is soluble in water at least to the extent necessary to dissolve an effective amount of the acid in water.

ORGANIC SOLVENT

Any suitable water-immiscible organic solvent may be used in the process of the invention. Examples of such solvents include: hydrocarbons such as benzene, toluene, and other water-immiscible aromatic solvents; hexane and other water-immiscible aliphatic solvents; halocarbons such as methylene chloride, chloroform, and other water-immiscible halocarbon solvents; oxygenated derivatives of hydrocarbons, such as methylisobutyl ketone and other water-immiscible oxo or oxy compounds; carboxylic esters such as ethylacetate and other water-insoluble ester solvents; and like solvents as known in the art. Preferably the solvent used has four to eight carbon atoms.

METAL SALT

The reaction mixture used in the process of the invention may comprise a metal salt, in addition to starting material, water, organic solvent and oxidizing agent, in which case the reaction product comprises a complex of that metal with the porphyrin produced in the process. Suitable metal salts for use in the process of the invention comprise zinc acetate, magnesium acetate, and other metal salts as known in the art to be reactive with hydroxyl-containing pyrrole compounds to form complexes of the metal with porphyrins.

PROPORTIONS OF REACTION MIXTURE COMPONENTS

The proportions of components of the reaction mixture of the process according to the invention are within the skill of the art to choose, in the light of the present specification. Typically the proportions will be in the following approximate ranges for every 1.0 gram of hydroxyl-containing pyrrolic starting material:

| Organic solvent | 100 to 1,000 milliliters |
| Water | 100 to 1,000 milliliters |
| Acid | 0.01 to 1 mole |
| Metal salt if present | 0.1 to 10 moles |

When a non-gaseous oxidizing agent is used, its amount will typically be in the approximate range from 1 to 20 moles grams per 1.0 gram of hydroxyl-containing pyrrolic starting material.

EXAMPLES

The following examples illustrate the invention. Table I gives examples of the process according to the invention, changing some of the variables from example to example.

TABLE I

| EX. | Solvent (ml) | Acid (ml) | 2-HMP (g) | $H_2O$ (ml) | DDQ (g) | % Yield | Comments |
|---|---|---|---|---|---|---|---|
| 1 | $CH_2Cl_2$ (100) | acetic (10) | 0.24 | 300 | 0.10 | 4.9 | |
| 2 | benzene (100) | acetic (10) | 0.25 | 300 | 0.10 | 2.9 | |
| 3 | $CHCl_3$ (100) | acetic (10) | 0.25 | 300 | 0.10 | 3.6 | |
| 4 | $CH_2Cl_2$ (100) | acetic (10) | 0.25 | 300 | 0.15 | 6.0 | 0.1 g Zn acetate |
| 5 | $CH_2Cl_2$ (200) | acetic (10) | 0.26 | 300 | 0.16 | 8.3 | |
| 6 | $CH_2Cl_2$ (100) | acetic (10) | 0.28 | 150 | 0.17 | 5.4 | |
| 7 | $CH_2Cl_2$ (100) | acetic (10) | 0.27 | 300 | 0.17 | 7.5 | 1 g Mg acetate |
| 8 | MIBK (100) | acetic (10) | 0.25 | 300 | 0.19 | 12.1 | |
| 9 | MIBK (100) | acetic (10) | 0.30 | 150 | 0.18 | 10.4 | |
| 10 | MIBK (100) | acetic (10) | 0.29 | 300 | 0.20 | 8.7 | 1. g Zn acetate |
| 11 | ethyl acetate (100) | acetic (10) | 0.26 | 300 | 0.20 | 9.0 | |
| 12 | MIBK (100) | acetic (5) | 0.27 | 300 | 0.22 | 12.0 | |
| 13 | MIBK (100) | formic (1) | 0.25 | 300 | 0.22 | 10.9 | |
| 14 | MIBK (100) | acetic (1) | 0.28 | 300 | 0.23 | 13.6 | |
| 15 | MIBK (100) | acetic (0.05) | 0.28 | 300 | 0.22 | 12.4 | |
| 16 | MIBK (100) | acetic (1) | 0.25 | 300 | 0.45 | 15.3 | |
| 17 | MIBK (100) | acetic (1) | 0.26 | 300 | 0.44 | 15.1 | |
| 18 | MIBK (100) | benzoic (2) | 0.25 | 300 | 0.45 | 10.0 | |

The reactions in Examples 1–18 were run at room temperature for 2 hr. DDQ was added and the mixture was heated to 60° C. for 30 min. The organic phase was separated, neutralized with sodium bicarbonate, and filtered through alumina. The solvent was evaporated and the solid porphin dried and weighed. The yields were based on pure 2-HMP and verified by UV spectrophotometric analyses.

2-HMP=2-hydroxymethylpyrrole

DDQ=2,3-dichloro-5,6-dicyano-1,4-benzoquinone

MIBK=methylisobutylketone or 4-methyl-2-pentanone

The organic solvents used in these runs were methylene chloride (Runs 1, 4, 5, 6, 7), benzene (Run 2), chloroform (Run 3), methylisobutylketone (Runs 8, 9, 10 and 12 through 18), and ethylacetate (Run 11).

The aqueous acid catalyst used in these runs was acetic acid, except for Run 13, in which formic acid was used, and Run 18 in which benzoic acid was used.

EXAMPLE 19

0.25 gram of 2-(1'-hydroxyethyl)pyrrole is dissolved in 100 ml of MIBK and added over 10 minutes to a stirring solution of 1 ml of glacial acetic acid in 300 ml of water. Air is bubbled through this stirred solution for 24 hours at room temperature. The two phases are separated and the organic layer is added to an equal volume of chloroform. The solution is filtered through a bed of neutral alumina and the solvent is removed by rotary evaporation producing nearly pure meso-tetramethylporphine.

EXAMPLE 20

0.25 g of 2-(1'-hydroxyphenyl)pyrrole is dissolved in 100 ml of MIBK and added over 120 minutes to a stirring solution of 1 ml of glacial acetic acid in 300 ml of water. After 2 hours of stirring at room temperature, 0.45 g of DDQ is added to the two phase mixture which is heated with stirring to 60° C. for 30 minutes. After cooling the two phases are neutralized with sodium bicarbonate then separated after the addition of 100 ml of chloroform. The organic layer is passed through a filter bed of neutral alumina producing nearly pure meso-tetraphenylporphine.

The invention claimed is:

1. Process for preparing a porphyrin which comprises contacting a hydroxyl-containing pyrrolic compound with a reaction mixture comprising more than one phase and comprising said pyrrole, an aqueous solution of an acid, a water-immiscible organic solvent and an oxidizing agent under conditions to form a porphyrin.

2. Process according to claim 1 wherein said pyrrole is a 2-hydroxyalkyl pyrrole.

3. Process according to claim 2 wherein said pyrrole is 2-hydroxymethyl pyrrole.

4. Process according to claim 1 wherein said solvent is a ketone.

5. Process according to claim 4 wherein said solvent is methylisobutyl ketone.

6. Process according to claim 1 wherein said solvent is an ester.

7. Process according to claim 6 wherein said solvent is ethyl acetate.

8. Process according to claim 1 wherein said solvent is a hydrocarbon.

9. Process according to claim 8 wherein said solvent is a cyclic hydrocarbon.

10. Process according to claim 9 wherein said solvent is benzene.

11. Process according to claim 1 wherein said acid is an acyclic organic acid.

12. Process according to claim 11 wherein said acid is formic acid, acetic acid or propionic acid.

13. Process according to claim 1 wherein said acid is an aromatic acid.

14. Process according to claim 13 wherein said acid is benzoic acid.

15. Process according to claim 1 wherein said oxidizing agent is molecular oxygen.

16. Process according to claim 1 wherein said oxidizing agent is an organic oxidant.

17. Process according to claim 16 wherein said oxidizing agent is a quinone.

18. Process according to claim 17 wherein said oxidizing agent is 2,3-dichloro-5,6-dicyano-1,4-benzoquinone.

19. Process according to claim 1 wherein said reaction mixture also comprises a metal salt.

20. Process according to claim 19 wherein said salt is a zinc salt.

21. Process according to claim 20 wherein said salt is zinc acetate.

22. Process according to claim 19 wherein said salt is a magnesium salt.

23. Process according to claim 22 wherein said salt is magnesium acetate.

24. Process according to claim 1 wherein said condensation conditions comprise temperature in the range from about 0° C. up to about 100° C.

25. Process according to claim 1 wherein said hydroxyl-containing pyrrolic compound is 2-hydroxymethylpyrrole.

26. Process according to claim 1 wherein said hydroxyl-containing pyrrolic compound is 2-(1'-hydroxyethylpyrrole).

27. Process according to claim 1 wherein said hydroxyl-containing pyrrolic compound is 2-(1'-hydroxyphenyl) pyrrole.

* * * * *